US009775792B2

(12) United States Patent
Liu et al.

(10) Patent No.: US 9,775,792 B2
(45) Date of Patent: *Oct. 3, 2017

(54) ORAL CARE PRODUCTS COMPRISING A TETRABASIC ZINC-AMINO ACID-HALIDE COMPLEX

(71) Applicant: Colgate-Palmolive Company, Piscataway, NJ (US)

(72) Inventors: Zhiqiang Liu, Bridgewater, NJ (US); Long Pan, Cherry Hill, NJ (US); Ying Yang, Monmouth Junction, NJ (US); Guofeng Xu, Plainsboro, NJ (US); Michael A. Stranick, Bridgewater, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/653,882

(22) PCT Filed: Dec. 19, 2012

(86) PCT No.: PCT/US2012/070521
§ 371 (c)(1),
(2) Date: Jun. 19, 2015

(87) PCT Pub. No.: WO2014/098825
PCT Pub. Date: Jun. 26, 2014

(65) Prior Publication Data
US 2015/0328111 A1 Nov. 19, 2015

(51) Int. Cl.
A61K 8/44 (2006.01)
A61K 8/20 (2006.01)
A61K 8/27 (2006.01)
A61K 8/21 (2006.01)
A61Q 11/00 (2006.01)

(52) U.S. Cl.
CPC ............... *A61K 8/27* (2013.01); *A61K 8/20* (2013.01); *A61K 8/21* (2013.01); *A61K 8/44* (2013.01); *A61Q 11/00* (2013.01); *A61K 2800/58* (2013.01); *A61K 2800/92* (2013.01)

(58) Field of Classification Search
None
See application file for complete search history.

(56) References Cited

U.S. PATENT DOCUMENTS

| | | |
|---|---|---|
| 2,503,280 A | 4/1950 | Lockwood |
| 2,507,088 A | 5/1950 | Bradley |
| 2,527,686 A | 10/1950 | Sandberg |
| 2,893,918 A | 7/1959 | Abramson |
| 3,260,744 A | 7/1966 | Kenkichi |
| 3,320,174 A | 5/1967 | Rubinfeld |
| 3,372,188 A | 3/1968 | Terence |
| 3,535,421 A | 10/1970 | Briner |
| 3,538,230 A | 11/1970 | Morton |
| 3,678,154 A | 7/1972 | Briner |
| 3,741,911 A | 6/1973 | Shane |
| 3,862,307 A | 1/1975 | Giulio |
| 3,937,807 A | 2/1976 | Haefele |
| 3,941,818 A | 3/1976 | Abdel-Monem |
| 3,959,458 A | 5/1976 | Agricola et al. |
| 4,051,234 A | 9/1977 | Gieske et al. |
| 4,316,824 A | 2/1982 | Pancheri |
| 4,339,432 A * | 7/1982 | Ritchey .................... A61K 8/27 424/49 |
| 4,340,583 A | 7/1982 | Wason |
| 4,487,757 A | 12/1984 | Kiozpeoplou |
| 4,565,693 A | 1/1986 | Marschner |
| 4,599,152 A | 7/1986 | Ashmead |
| 4,684,528 A * | 8/1987 | Godfrey ................. A23G 3/368 424/49 |
| 4,687,663 A | 8/1987 | Schaeffer |
| 4,842,847 A | 6/1989 | Amjad |
| 4,866,161 A | 9/1989 | Sikes et al. |
| 4,885,155 A | 12/1989 | Parran, Jr. et al. |
| 5,004,597 A | 4/1991 | Majeti et al. |
| 5,061,815 A | 10/1991 | Leu |
| 5,156,845 A | 10/1992 | Grodberg |
| 5,188,821 A | 2/1993 | Gaffar et al. |
| 5,192,531 A | 3/1993 | Gaffar et al. |
| 5,504,055 A | 4/1996 | Hsu |
| 5,643,559 A | 7/1997 | Eigen et al. |
| 5,698,724 A | 12/1997 | Anderson et al. |
| 5,707,679 A | 1/1998 | Nelson |
| 5,714,447 A | 2/1998 | Jones et al. |
| 5,911,978 A | 6/1999 | Carr et al. |
| 5,993,784 A | 11/1999 | Hill |
| 6,121,315 A | 9/2000 | Nair et al. |

(Continued)

FOREIGN PATENT DOCUMENTS

| | | |
|---|---|---|
| CN | 101289412 A * | 10/2008 |
| CN | 101316572 | 12/2008 |

(Continued)

OTHER PUBLICATIONS

English translation of CN 101289412 A from Espacenet/Google.*
Anonymous, "Zinc Lauryl Ether Sulphate, A New Approach to Skincare,", Apr. 2004, Retrieved from Internet, http://www.erwebhosting.it/zsi/repository/Zinc%20Lauryl%20Ether%20Sulphate%20A%20new%20approach%20to%20skin%20care.pdf, Retrieved Sep. 26, 2013.
Deschaume et al., "Interactions of aluminum hydrolytic species with biomolecules," New Journal of Chemistry, 2008, 32:1346-1353.

(Continued)

*Primary Examiner* — Isaac Shomer
*Assistant Examiner* — Michael P Cohen

(57) ABSTRACT

Described herein are oral care compositions comprising a tetrabasic zinc halide and an amino acid; along with methods of making and using the same.

10 Claims, No Drawings

(56) References Cited

U.S. PATENT DOCUMENTS

| | | | |
|---|---|---|---|
| 6,156,293 | A | 12/2000 | Jutila et al. |
| 6,607,711 | B2 | 8/2003 | Pedersen |
| 6,685,920 | B2 | 2/2004 | Baig et al. |
| 6,969,510 | B2 | 11/2005 | Holerca et al. |
| 8,067,627 | B2 | 11/2011 | Newsome et al. |
| 8,247,398 | B2 | 8/2012 | Goel |
| 2004/0033916 | A1 | 2/2004 | Kuzmin et al. |
| 2004/0042978 | A1 | 3/2004 | Embro |
| 2004/0122088 | A1 | 6/2004 | Newsome et al. |
| 2004/0198998 | A1 | 10/2004 | Holerca et al. |
| 2006/0024252 | A1 | 2/2006 | Esposito et al. |
| 2007/0071698 | A1 | 3/2007 | Doss |
| 2009/0220444 | A1 | 9/2009 | Teckenbrock et al. |
| 2010/0021573 | A1 | 1/2010 | Gonzalez et al. |
| 2010/0266480 | A1 | 10/2010 | Huang |
| 2010/0330163 | A1 | 12/2010 | Soparkar |
| 2011/0076309 | A1 | 3/2011 | Misner et al. |
| 2011/0229536 | A1 | 9/2011 | Kvitnitsky et al. |
| 2013/0017240 | A1 | 1/2013 | Porter et al. |
| 2014/0170086 | A1 | 6/2014 | Pan et al. |

FOREIGN PATENT DOCUMENTS

| | | | |
|---|---|---|---|
| CN | 101606639 | | 12/2009 |
| CN | 102811698 | | 12/2012 |
| CN | 103156073 | | 6/2013 |
| CN | 103535536 | | 1/2014 |
| DE | 735096 | | 5/1943 |
| EP | 0083486 | | 12/1982 |
| EP | 0108937 | | 5/1984 |
| EP | 0508524 | | 10/1992 |
| EP | 0514553 | | 11/1992 |
| EP | 0842664 | | 5/1998 |
| EP | 1021158 | | 7/2000 |
| EP | 1064946 | | 1/2001 |
| EP | 1203575 | | 5/2002 |
| EP | 1319394 | | 6/2003 |
| EP | 1935395 | | 6/2008 |
| EP | 1529775 | | 5/2011 |
| FR | 2241301 | | 3/1975 |
| GB | 2052978 | | 2/1981 |
| GB | 2109685 | | 6/1983 |
| GB | 2243775 | | 11/1991 |
| GB | 2243775 | A * | 11/1991 ............... A61K 8/19 |
| JP | S57-158724 | | 9/1982 |
| JP | 2040175790 | | 6/2004 |
| JP | 2009084201 | | 4/2009 |
| JP | 2010132639 | | 6/2010 |
| WO | WO86/00004 | | 1/1986 |
| WO | WO9917735 | | 4/1999 |
| WO | WO 00/28952 | | 5/2000 |
| WO | WO0169087 | | 9/2001 |
| WO | WO2004054531 | | 7/2004 |
| WO | WO2004/064536 | | 8/2004 |
| WO | WO2007063507 | | 6/2007 |
| WO | WO2011053291 | | 5/2011 |
| WO | WO2011/088199 | | 7/2011 |
| WO | WO2011/123123 | | 10/2011 |
| WO | WO2014/098813 | | 6/2014 |
| WO | WO2014/098814 | | 6/2014 |
| WO | WO2014/098818 | | 6/2014 |
| WO | WO2014/098819 | | 6/2014 |
| WO | WO2014/098821 | | 6/2014 |
| WO | WO2014/098822 | | 6/2014 |
| WO | WO2014/098824 | | 6/2014 |
| WO | WO2014/099164 | | 6/2014 |
| WO | WO2014/099165 | | 6/2014 |
| WO | WO2014/099166 | | 6/2014 |
| WO | WO2014/099167 | | 6/2014 |
| WO | WO2014098825 | | 6/2014 |
| WO | WO2014098826 | | 6/2014 |
| WO | WO2014098828 | | 6/2014 |
| WO | WO2014098829 | | 6/2014 |
| WO | WO2014099039 | | 6/2014 |
| WO | WO2014099226 | | 6/2014 |
| WO | WO2014204439 | | 12/2014 |

OTHER PUBLICATIONS

European Food Safety Authority, "Scientific Opinion on the safety and efficacy of tetra-basic zinc chloride for all animal species," EFSA Journal, 2012, 10(5):2672.

Hartwell et al., "Preparation and characterization of tyrosine and lysine metal chelate polyesters and polyamides", J. of the American Chem. Society, Mar. 1970, 92(5):1284-1289.

International Search Report and Written Opinion for International Application No. PCT/US2012/070489 dated Oct. 22, 2013.

International Search Report and Written Opinion for International Application No. PCT/US2012/070492 dated Oct. 22, 2013.

International Search Report and Written Opinion for International Application No. PCT/US2012/070498 dated Sep. 4. 2013.

International Search Report and Written Opinion for International Application No. PCT/US2012/070501 dated Oct. 21, 2013.

International Search Report and Written Opinion for International Application No. PCT/US2012/070505 dated Nov. 20, 2013.

International Search Report and Written Opinion for International Application No. PCT/US2012/070506 dated Oct. 14, 2013.

International Search Report and Written Opinion for International Application No. PCT/US2012/070513 dated Oct. 14, 2013.

International Search Report and Written Opinion for International Application No. PCT/US2012/070521 dated Sep. 30, 2013.

International Search Report and Written Opinion for International Application No. PCT/US2012/070525 dated Sep. 27, 2013.

International Search Report and Written Opinion for International Application No. PCT/US2012/070528 dated Sep. 30, 2013.

International Search Report and Written Opinion for International Application No. PCT/US2012/070534 dated Sep. 26, 2013.

International Search Report and Written Opinion for International Application No. PCT/US2012/070537 dated Oct. 11, 2013.

International Search Report and Written Opinion for International Application No. PCT/US2013/046268 dated Apr. 22, 2014.

International Search Report and Written Opinion for International Application No. PCT/US2013/050845 dated Aug. 13, 2014.

International Search Report and Written Opinion for International Application No. PCT/US2013/0688852 dated Nov. 10, 2014.

International Search Report and Written Opinion for International Application No. PCT/US2013/068854 dated Oct. 20, 2014.

International Search Report and Written Opinion for International Application No. PCT/US2013/068859 dated Aug. 4, 2014.

International Search Report and Written Opinion for International Application No. PCT/US2013/068860 dated Oct. 22, 2014.

International Search Report and Written Opinion for International Application No. PCT/US2013/070932 dated Jul. 24, 2014.

International Search Report and Written Opinion for International Application No. PCT/US2014/042947 dated Aug. 22, 2014.

International Search Report and Written Opinion for International Application No. PCT/US2014/042948 dated Aug. 26, 2014.

International Search Report and Written Opinion for International Application No. PCT/US2014/043051 dated Feb. 18, 2015.

Kondrot, "The Importance of Zinc," http://www.healingtheeye.com/Articles/zinc.html, Feb. 21, 2012.

Liang et al., "In vitro scratch assay: a convenient and inexpensive method for analysis of cell migration in vitro," Nature Protocols, 2007, 2(2):329-333.

Liu et al., "The research on zinc coordination No. 5 odd structure in zinc complex with L-lysine," J. Molecular Science, 2000, 16(2):114-117, abstract only in English.

Lu et al., "Albumin as a zinc carrier: properties of its high-affinity zinc-binding site". Biochem. Soc. Trans., 2008, 36:1317-1321.

Lynch, "Zinc in the mouth, its interactions with dental enamel and possible effects on caries: a review of the literature.," Int. Dent. J., Aug. 2011, Suppl 3:46-54.

Mavromichalis et al., "Growth-promoting efficacy of pharmacological doses of tetrabasic zinc chloride in diets for nursery pigs," Canadian Journal of Animal Science, pp. 387-391, Jan. 2001.

(56) References Cited

OTHER PUBLICATIONS

McAuliffe et al., "Metal complexes of sulphur-containing amino acids," Inorganica Chimica Acta Reviews, Dec. 1972, 6:103-121.
Moore et al., "Antibacterial activity of gutta-percha cones attributed to the zinc oxide component," Oral Surgery: 1982, 53:508-517.
Mosmann, "Rapid colorimetric assay for cellular growth and survival: Application to proliferation and cytotoxicity assays," J. Immunol. Methods, 1983, 65:55-63.
Pashley et al. Dentin permeability effects of desensitizing dentifries in vitro. J Periodontol. 1984:55(9):522-525.
Prasad, "Zinc:role in immunity, oxidative stress and chronic inflammation,"Current Opinion in Clinical Nutrition and Metabolic Care, 2009, 12:646-652.
Rigano, I.., Zinc Lauryl Ether Sulphate—A New Approach to Skin Care, SOFW Journal, Apr. 2004, 128:26-33.
Schmetzer et al., "Walfingite, ε-Zn(OH)2, and simonkolleite, Zn5(OH)8C12•H2O, two new minerals from Richelsdorf Hesse, F.R.G.," N. Jb. Miner. Mh., Apr. 1985, pp. 145-154.
Seil et al., "Antibacterial effect of zinc oxide nanoparticles combined with ultrasound," Nanotechology,2012, 23:495101.
Soderling et al., "Betaine-coniaining toothpaste relieves subjective symptoms of dry mouth," Acta Odontol. Scand., Apr. 1998, 56(2):65-9.
Stewart et al., "Interdomain zinc site on human albumin," PNAS, 2003, 100(7):3701-3706.
Tian et al., "Using DGGE profiling to develop a novel culture medium suitable for oral microbial communities," Molecular Oral Microbiology, 2010, 25(5):357-367.
Twetman et al., 2003, "Caries-preventative effect of fluoride toothpaste a systematic review," Acta Odontol Scand., Dec. 2003, 61(6):347-55.
Wachi et al., "Antibacterial compsn. Zinc oxide—solubilized by amino acid, amino acid hydrochloride and/or amino acid alkali metal salt," Sep. 1982, vol. 1982(45).
Wallhausser et al., "Antimicrobial Preservatives in Europe: Experience with preservatives used in pharmaceuticals and cosmetics," Develop. Biol. Standard, 1974, 24:9-28.
Yao et al., "An investigation of zirconium(IV)-glycine(CP-2) hybrid complex in bovine serum albumin protein matrix under varying conditions," J. of Materials Chemistry, 2011, 21:19005-19012.
Yousef et al., "In vitro antibacterial activity and minimum inhibitory concentration of zinc oxide and nano-particle zinc oxide against pathogenic strains," J. of Health Sciences, 2012, 2(4):38-42.
Zhu et al., "Synthesis and Crystal Structure of [Zn+{H2N(CH2)4CH(NH2)COONa}2SO4-] •H20," Chinese Science Bulletin, Sep. 1990, 35(18):1521-1525.
Batal et al., "Zinc Bioavailability in Tetrabasic Zinc Chloride and the Dietary Zinc Requirement of Young Chicks Fed a Soy Concentrate Diet," Poultry Science, 2001, 80:87-90.
Rulai et al., "Prevention and Treatment of Zinc Deficiency in Children," Published by Zhejiang Science and Technology Press, Chapter 4, Feb. 2004.

\* cited by examiner

ORAL CARE PRODUCTS COMPRISING A TETRABASIC ZINC-AMINO ACID-HALIDE COMPLEX

CROSS-REFERENCE TO RELATED APPLICATIONS

This application is a United States National Stage Application under 35 U.S.C. §371 of International Application PCT/US2012/070521, filed on Dec. 19, 2012, the contents of which is hereby incorporated by reference in its entirety.

BACKGROUND

Heavy metal ions, such as zinc, are resistant to acid attack. Zinc ranks above hydrogen in the electrochemical series, so that metallic zinc in an acidic solution will react to liberate hydrogen gas as the zinc passes into solution to form di-cations, $Zn^{2+}$. Zinc has been shown to have antibacterial properties in plaque and caries studies.

Soluble zinc salts, such as zinc citrate, have been used in dentifrice compositions, see, e.g., U.S. Pat. No. 6,121,315, but have several disadvantages. Zinc ions in solution impart an unpleasant, astringent mouthfeel, so formulations that provide effective levels of zinc, and also have acceptable organoleptic properties, have been difficult to achieve. Finally, the zinc ions will react with anionic surfactants such as sodium lauryl sulfate, thus interfering with foaming and cleaning.

Tetrabasic zinc chloride (TBZC), is a zinc hydroxy compound with chemical formula $Zn_5(OH)_8Cl_2 \cdot H_2O$. It is also referred to as zinc chloride hydroxide monohydrate, basic zinc chloride, zinc hydroxychloride, or zinc oxychloride. It occurs naturally as the mineral simonkolleite. Unlike zinc chloride, TBZC is insoluble in water. TBZC has been suggested for use in oral care compositions, see e.g., GB2243775A, but such formulations do not deliver zinc efficiently to the teeth due to the insolubility of TBZC.

While the prior art discloses the use of various oral compositions for the treatment of dentinal hypersensitivity, dental caries, and enamel erosion and demineralization, there is still a need for additional compositions and methods which provide improved performance in such treatments.

SUMMARY

While TBZC is substantially insoluble in prior art formulations, it has now been discovered that tetrabasic zinc chloride can form a soluble complex with an amino acid. When placed in formulation, this complex provides an effective concentration of zinc ions to the enamel, thereby protecting against erosion, reducing bacterial colonization and biofilm development, and providing enhanced shine to the teeth. Moreover, upon use, the formulation provides a precipitate which can plug the dentinal tubules, thereby reducing the sensitivity of the teeth. This is unexpected, in view of the poor solubility of TBZC. While providing efficient delivery of zinc in comparison to conventional formulations with insoluble TBZC, the formulations comprising the TBZC-amino acid complex do not exhibit the poor taste and mouthfeel, poor fluoride delivery, and poor foaming and cleaning associated with conventional zinc-based oral care products using soluble zinc salts.

The invention thus provides oral care compositions, for example mouthwash, oral gel or dentifrice compositions that comprise TBZC in combination with an amino acid. In one embodiment the composition further comprises an amino acid, e.g., a basic amino acid. The compositions may optionally further comprise a fluoride source and or an additional phosphate source. The compositions may be formulated in a suitable oral care formulation e.g., a conventional dentifrice, oral gel or mouthwash base, e.g., comprising one or more abrasives, surfactants, foaming agents, vitamins, polymers, enzymes, humectants, thickeners, antimicrobial agents, preservatives, flavorings, and/or colorants.

The invention further provides methods of using the compositions of the invention to reduce and inhibit acid erosion of the enamel, clean the teeth, reduce bacterially-generated biofilm and plaque, reduce gingivitis, inhibit tooth decay and formation of cavities, and reduce dentinal hypersensitivity, comprising applying a composition of the invention to the teeth.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

The present invention therefore provides, in a first embodiment, an oral care composition (Composition 1), comprising a tetrabasic zinc chloride (TBZC) in complex with an amino acid; e.g., 1.1. Composition 1 wherein the amino acid is selected from lysine, glycine and arginine, in free or orally acceptable acid addition salt form, e.g., hydrochloride form.
1.2. Composition 1 or 1.1 wherein the amino acid is a basic amino acid, e.g., arginine or lysine, in free or orally acceptable salt form.
1.3. Any of the foregoing compositions wherein the TBZC-amino acid complex is formed, in whole or in part, in situ after the composition is applied.
1.4. Any of the foregoing compositions wherein the TBZC-amino acid complex is formed, in whole or in part, in situ after the composition is formulated.
1.5. Any of the foregoing compositions, wherein the amino acid is lysine.
1.6. Any of the foregoing compositions, wherein the zinc amino acid halide and/or zinc amino acid halide precursors are present in an amount of 0.05 to 10% by weight of the composition, optionally at least 0.1, at least 0.2, at least 0.3, at least 0.4, at least 0.5, at least 1, at least 2, at least 3, or at least 4 up to 10% by weight of the composition.
1.7. Any of the foregoing compositions, wherein TBZC is present in an amount of 0.05 to 10% by weight of the composition, optionally at least 0.1, at least 0.2, at least 0.3, at least 0.4, at least 0.5, at least 1, at least 2, at least 3, or at least 4 up to 10% by weight of the composition.
1.8. Any of the foregoing compositions, wherein amino acid hydrohalide is present in an amount of 0.05 to 30% by weight of the composition, optionally at least 0.1, at least 0.2, at least 0.3, at least 0.4, at least 0.5, at least 1, at least 2, at least 3, at least 4, at least 5, at least 10, at least 15, at least 20 up to 30% by weight.
1.9. Any of the foregoing compositions, wherein TBZC and amino acid hydrohalide are present in amounts such that if combined into the zinc amino acid halide, the zinc amino acid halide would be present in an amount of 0.05 to 10% by weight of the composition.

1.10. Any of the foregoing compositions, wherein a molar ratio of zinc to amino acid is 2:1 to 1:4, optionally 1:1 to 1:4, 1:2 to 1:4, 1:3 to 1:4, 2:1 to 1:3, 2:1 to 1:2, 2:1 to 1:1, or 1:3

1.11. Any of the foregoing compositions, wherein a total amount of zinc present in the composition is 0.05 to 10% by weight.

1.12. Any of the foregoing compositions, wherein the halide is selected from the group consisting of chlorine, bromine, and iodine.

1.13. Any of the foregoing compositions, wherein the zinc amino acid halide is zinc lysine chloride.

1.14. Any of the foregoing compositions, in an anhydrous carrier.

1.15. Any of the foregoing compositions, which is anhydrous composition comprising TBZC and amino acid hydrohalide.

1.16. Any of the foregoing compositions comprising an amino acid hydrohalide which is lysine hydrochloride.

1.17. Any of the foregoing compositions comprising a zinc amino acid halide formed from TBZC and an amino acid hydrohalide.

1.18. Any of the foregoing compositions wherein the halide is chloride.

1.19. Any of the foregoing compositions wherein the amino acid is lysine.

1.20. Any of the foregoing compositions wherein the zinc amino acid halide is a zinc lysine chloride complex (e.g., $(ZnLys_2Cl)^+Cl^-$ or $(ZnLys_3)^{2+}Cl_2$) or zinc arginine chloride complex.

1.21. Any of the foregoing compositions in the form of a toothpaste, gel, mouthwash, powder, cream, strip, or gum.

1.22. Any of the foregoing compositions in an orally acceptable base, e.g., a mouthwash, gel, or dentifrice base.

1.23. Any of the foregoing compositions in the form of a dentifrice, e.g., wherein the TBZC-amino acid complex is present in an effective amount, e.g., in an amount of 0.5-4% by weight of zinc, e.g., about 1-3% by weight of zinc, in a dentifrice base.

1.24. Composition 1.1, wherein the dentifrice base comprises an abrasive, e.g., an effective amount of a silica abrasive, e.g., 10-30%, e.g., about 20%.

1.25. Composition 1 in the form of a mouthwash, e.g., wherein the TBZC-amino acid complex is present in an effective amount, e.g., in an amount of 0.5-4% by weight of zinc, e.g., about 1-3% by weight of zinc.

1.26. Any of the foregoing compositions further comprising an effective amount of a fluoride ion source, e.g., providing 500 to 3000 ppm fluoride.

1.27. Any of the foregoing compositions further comprising an effective amount of fluoride, e.g., wherein the fluoride is a salt selected from stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof 1.28. Any of the preceding compositions comprising an effective amount of one or more alkali phosphate salts, e.g., sodium, potassium or calcium salts, e.g., selected from alkali dibasic phosphate and alkali pyrophosphate salts, e.g., alkali phosphate salts selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any of two or more of these, e.g., in an amount of 1-20%, e.g., 2-8%, e.g., ca. 5%, by weight of the composition.

1.29. Any of the foregoing compositions comprising buffering agents, e.g., sodium phosphate buffer (e.g., sodium phosphate monobasic and disodium phosphate).

1.30. Any of the foregoing compositions comprising a humectant, e.g., selected from glycerin, sorbitol, propylene glycol, polyethylene glycol, xylitol, and mixtures thereof, e.g. comprising at least 20%, e.g., 20-40%, e.g., 25-35% glycerin.

1.31. Any of the preceding compositions comprising one or more surfactants, e.g., selected from anionic, cationic, zwitterionic, and nonionic surfactants, and mixtures thereof, e.g., comprising an anionic surfactant, e.g., a surfactant selected from sodium lauryl sulfate, sodium ether lauryl sulfate, and mixtures thereof, e.g. in an amount of from about 0.3% to about 4.5% by weight, e.g. 1-2% sodium lauryl sulfate (SLS); and/or a zwitterionic surfactant, for example a betaine surfactant, for example cocamidopropylbetaine, e.g. in an amount of from about 0.1% to about 4.5% by weight, e.g. 0.5-2% cocamidopropylbetaine.

1.32. Any of the preceding compositions further comprising a viscosity modifying amount of one or more of polysaccharide gums, for example xanthan gum or carrageenan, silica thickener, and combinations thereof 1.33. Any of the preceding compositions comprising gum strips or fragments.

1.34. Any of the preceding compositions further comprising flavoring, fragrance and/or coloring.

1.35. Any of the foregoing compositions comprising an effective amount of one or more antibacterial agents, for example comprising an antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing; e.g., comprising triclosan or cetylpyridinium chloride.

1.36. Any of the foregoing compositions comprising an antibacterially effective amount of triclosan, e.g. 0.1-0.5%, e.g. about 0.3%.

1.37. Any of the preceding compositions further comprising a whitening agent, e.g., a selected from the group consisting of peroxides, metal chlorites, perborates, percarbonates, peroxyacids, hypochlorites, and combinations thereof.

1.38. Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate);

1.39. Any of the preceding compositions further comprising an agent that interferes with or prevents bacterial attachment, e.g., solbrol or chitosan.

1.40. Any of the preceding compositions further comprising a source of calcium and phosphate selected from (i) calcium-glass complexes, e.g., calcium sodium phosphosilicates, and (ii) calcium-protein complexes, e.g., casein phosphopeptide-amorphous calcium phosphate 1.41. Any of the preceding compositions further comprising a soluble calcium salt, e.g., selected from calcium sulfate, calcium chloride, calcium nitrate, calcium acetate, calcium lactate, and combinations thereof 1.42. Any of the preceding compositions further comprising a physiologically or orally acceptable potassium salt, e.g., potassium nitrate or potassium chloride, in an amount effective to reduce dentinal sensitivity.

1.43. Any of the foregoing compositions further comprising an anionic polymer, e.g., a synthetic anionic polymeric polycarboxylate, e.g., wherein the anionic polymer is selected from 1:4 to 4:1 copolymers of maleic anhydride or acid with another polymerizable ethylenically unsaturated monomer; e.g., wherein the anionic polymer is a methyl vinyl ether/maleic anhydride (PVM/MA) copolymer having an average molecular weight (M.W.) of about 30,000 to about 1,000,000, e.g. about 300,000 to about 800,000, e.g., wherein the anionic polymer is about 1-5%, e.g., about 2%, of the weight of the composition.

1.44. Any of the preceding compositions further comprising a breath freshener, fragrance or flavoring.

1.45. Any of the foregoing compositions, wherein the pH of the composition is approximately neutral, e.g., from pH 6 to pH 8 e.g., about pH 7.

1.46. Any of the forgoing compositions for use to reduce and inhibit acid erosion of the enamel, clean the teeth, reduce bacterially-generated biofilm and plaque, reduce gingivitis, inhibit tooth decay and formation of cavities, and reduce dentinal hypersensitivity.

In some embodiments, the present invention provides an oral care composition comprising a tetrabasic zinc halide and an amino acid.

The invention further provides methods to reduce and inhibit acid erosion of the enamel, clean the teeth, reduce bacterially-generated biofilm and plaque, reduce gingivitis, inhibit tooth decay and formation of cavities, and reduce dentinal hypersensitivity, comprising applying an effective amount of a composition of the invention, e.g., any of Composition 1, et seq. to the teeth.

The invention further provides a method of making a composition comprising a zinc amino acid halide, e.g., any of Composition 1, et seq. comprising combining zinc amino acid halide precursors selected from (a) tetrabasic zinc chloride and an amino acid, and/or (b) tetrabasic zinc chloride, and an amino acid in an aqueous base material.

The invention further provides a method of making a composition comprising a zinc amino acid halide, e.g., any of Composition 1, et seq. comprising combining zinc amino acid halide precursors selected from (a) tetrabasic zinc chloride and an amino acid halide, and/or (b) tetrabasic zinc chloride, an amino acid and a halogen acid in an aqueous base material.

For example, in various embodiments, the invention provides methods to (i) reduce hypersensitivity of the teeth, (ii) to reduce plaque accumulation, (iii) reduce or inhibit demineralization and promote remineralization of the teeth, (iv) inhibit microbial biofilm formation in the oral cavity, (v) reduce or inhibit gingivitis, (vi) promote healing of sores or cuts in the mouth, (vii) reduce levels of acid producing bacteria, (viii) to increase relative levels of non-cariogenic and/or non-plaque forming bacteria, (ix) reduce or inhibit formation of dental caries, (x), reduce, repair or inhibit pre-carious lesions of the enamel, e.g., as detected by quantitative light-induced fluorescence (QLF) or electrical caries measurement (ECM), (xi) treat, relieve or reduce dry mouth, (xii) clean the teeth and oral cavity, (xiii) reduce erosion, (xiv) whiten teeth; (xv) reduce tartar build-up, and/or (xvi) promote systemic health, including cardiovascular health, e.g., by reducing potential for systemic infection via the oral tissues, comprising applying any of Compositions 1, et seq. as described above to the oral cavity of a person in need thereof, e.g., one or more times per day. The invention further provides Compositions 1, et seq. for use in any of these methods.

The invention further provides the use of TBZC and an amino acid to make an oral care composition comprising a zinc amino acid halide.

The invention further provides (i) the use of a zinc amino acid halide made from TBZC (e.g., made from zinc amino acid halide precursors selected from (a) tetrabasic zinc chloride and an amino acid halide, and/or (b) tetrabasic zinc chloride, an amino acid and optionally halogen acid) to reduce and inhibit acid erosion of the enamel, clean the teeth, reduce bacterially-generated biofilm and plaque, reduce gingivitis, inhibit tooth decay and formation of cavities, and reduce dentinal hypersensitivity; (ii) the use of a zinc amino acid halide precursors selected from (a) tetrabasic zinc chloride and an amino acid halide, and/or (b) tetrabasic zinc chloride, an amino acid and optionally halogen acid in the manufacture of a composition to reduce and inhibit acid erosion of the enamel, clean the teeth, reduce bacterially-generated biofilm and plaque, reduce gingivitis, inhibit tooth decay and formation of cavities, and reduce dentinal hypersensitivity.

Without intending to be bound by theory, it is believed that the formation of the zinc amino acid halide proceeds via formation of the zinc halide then coordination of amino acid residues around a central zinc. Using reaction of TBZC with lysine hydrochloride in water as an example, the TBZC ($Zn_5(OH)_8Cl_2.H_2O$) can react with lysine and/or lysine.HCl to form a clear solution of Zn-lysine-chloride complex ($ZnLys_3Cl_2$), wherein $Zn^{2+}$ is located in an octahedral center coordinated with two oxygen and two nitrogen atoms in the equatorial plane coming from two lysine's carboxylic acids and amine groups respectively. The zinc is also coordinated to the third lysine via its nitrogen and carboxylic oxygen, at the apical position of the metal geometry.

In another embodiment, a zinc cation is complexes with two amino acid residues and two chloride residues. For example, where the amino acid is lysine, the complex has the formula $[Zn(C_6H_{14}N_2O_2)_2Cl]^+Cl^-$. In this complex, Zn cation is coordinated by two lysine ligands with two N atoms from $NH_2$ groups and O atoms from carboxylic groups in an equatorial plane. It displays a distorted square-pyramidal geometry with the apical position occupied by a $Cl^-$ atom. This novel structure gives rise to a positive cation moiety, to which a $Cl^-$ anion is combined to form an ionic salt.

Other complexes of TBZC and amino acid are possible, and the precise form is dependent in part on the molar ratios of the precursor compounds, e.g., if there is limited halide, halide-free complexes may form, e.g. $ZnOLys_2$, having a pyramid geometry, with the equatorial plane that is same as the above compound (Zn is bound to two oxygen and two nitrogen atoms from different lysines), wherein the top of the pyramid is occupied by an O atom.

Mixtures of complexes and/or additional complex structures, e.g., involving multiple zinc ions based on the TBZC structure, are possible and contemplated within the scope of the invention. When the complexes are in solid form, they may form crystals, e.g. in hydrated form.

Irrespective of the precise structure of the complex or complexes, however, the interaction of the zinc and the amino acid converts the insoluble TBZC to a highly soluble complex. With increasing dilution in water, however, the complex disassociates, and the zinc ion reverts to insoluble zinc oxide or TBZC. This dynamic is unexpected and facilitates deposition of the zinc precipitate on the teeth upon administration, which acts to occlude the dentinal tubules, thereby reducing hypersensitivity, and also providing zinc to the enamel, which reduces acid erosion, biofilm and plaque formation.

It will be understood that other amino acids can be used in place of lysine in the foregoing scheme. It will also be understood that, although the zinc, amino acid and halide may be primarily in the form of precursor materials or in the form of a complex, there may be some degree of equilibrium, so that the proportion of material which is actually in complex compared to the proportion in precursor form may vary depending on the precise conditions of formulation, concentration of materials, pH, presence or absence of water, presence or absence of other charged molecules, and so forth.

The actives can be delivered in the form of any oral care formulations, for example a toothpaste, gel, mouthwash, powder, cream, strip, gum, or any other known in the art.

If the actives are delivered in the form of a mouthwash, a person desiring the benefits rinses with the stock solution and natural dilution of the stock solution by saliva will initiate the precipitation of the zinc. Alternatively, the person can mix the stock solution with appropriate amount of an aqueous diluent (such as approximately 1 part stock solution and 8 parts water for the TBZC-lysine samples), and rinse with the mixture.

In another embodiment, the mixture is prepared and immediately transferred into a retaining tray, such as those used in holding whitening gels, and the person can wear the tray for the effective period of time. The teeth that are in contact with the mixture will be treated. For use with retaining tray, the mixture can be in the form of a low-viscosity liquid or a gel.

In another embodiment, the stock solution, or a mixture of stock solution with water, is applied to the teeth in a gel formulation, e.g., wherein the gel can stay on the tooth for an extended period of time for effective treatment.

In another embodiment, the active is provided in a toothpaste. Upon brushing, the active is diluted by saliva and water, leading to precipitation and the formation of deposits and occluding particles.

The rate of precipitation from the formulation can be modulated by adjusting concentration of the complex in the stock solution, and changing the ratio of the stock to water. A more diluted formula leads to faster precipitation and is thus preferred when a fast treatment is desired.

The benefits of the oral care compositions of the invention are numerous. By providing zinc ions and zinc containing compounds that can release zinc ions in oral cavities, the oral care compositions of the invention provide antimicrobial, antiplaque, antigingivitis, anti-malodor, anticaries, and anticalculus benefits. The occluding particles and the surface deposits are compounds containing zinc (particularly ZnO), as well as other zinc derivatives which can release zinc ions into oral cavities and provide the various benefits as recognized above. Additional benefits include but are not limited to anti-attachment, anti-periodontitis and anti-bone loss, as well as promotion of wound healing.

A second benefit is the antierosive properties of zinc ions, which form antierosive deposits on tooth surfaces through oxidation and hydrolysis. The surface deposits, as well as the occluding particles, can react with and neutralize acids, thus protecting the dental surface from the erosive effects of the acids. In this regard, the more surface depositions/occlusion the treatments lead to, the more efficacious the treatments are, and therefore TBZC-arginine and TBZC-lysine are preferred. It is also noted that when the surface deposits and occluding particles neutralize acids, beneficial zinc ions and amino acids (infra) can be released, providing oral care benefits other than anti-erosion.

A third benefit is anti-sensitivity benefit as a result of the occlusion. Occlusion of dentin tubules leads to sensitivity relief.

A fourth benefit is the benefit associated with amino acids. The occluding particles and surface deposits contain the corresponding amino acids, such as arginine and lysine. These amino acids provide multiple benefits. For example, basic amino acids lead to higher pH of the plaque and can provide anticaries benefits. In addition, it is also expected that arginine can enhance the activity of arginolytic bacteria, leading to a more healthy plaque. Arginine is also known to promote wound healing and collagen integrity.

The composition can include the zinc amino acid halide and/or precursors thereof. Precursors, which can react in situ with water to form the zinc amino acid halide, include (i) TBZC and an amino acid hydrohalide, or (ii) zinc chloride and amino acid, or (iii) a zinc ion source, an amino acid, and a halogen acid, or (iv) combinations of (i), (ii), and/or (iii). In one embodiment, the zinc amino acid halide can be prepared at room temperature by mixing the precursors in a solution, such as water. The in situ formation provides ease of formulation. The precursors can be used instead of first having to form the zinc amino acid halide. In another embodiment, the water permitting formation of the zinc amino acid halide from the precursor comes from saliva and/or rinsing water that comes into contact with the composition after application.

The zinc amino acid halide is a water soluble complex formed from the halide acid addition salt of zinc (e.g., zinc chloride) and an amino acid, or from the halide acid addition salt of an amino acid (e.g., lysine hydrochloride) and zinc ion source, e.g., TBZC, and/or from combination of all three of a halogen acid, an amino acid, and a zinc ion source.

Examples of amino acids include, but are not limited to, the common natural amino acids, e.g.: lysine, arginine, histidine, glycine, serine, threonine, asparagine, glutamine, cysteine, selenocysteine, proline, alanine, valine, isoleucine, leucine, methionine, phenylalanine, tyrosine, tryptophan, aspartic acid, and glutamic acid. In some embodiments the amino acid is a neutral or acidic amino acid, e.g., glycine.

As seen from the examples below, the precipitation of zinc from the complex upon dilution with water is most notable when the complex is formed from a basic amino acid. Thus, where precipitation upon dilution is desired, a basic amino acid may be preferred. In some embodiments, therefore, the amino acid is a basic amino acid. By "basic amino acid" is meant the naturally occurring basic amino acids, such as arginine, lysine, and histidine, as well as any basic amino acid having a carboxyl group and an amino group in the molecule, which is water-soluble and provides an aqueous solution with a pH of about 7 or greater. Accordingly, basic amino acids include, but are not limited to, arginine, lysine, citrulline, ornithine, creatine, histidine, diaminobutanoic acid, diaminoproprionic acid, salts thereof or combinations thereof. In certain embodiments, the amino acid is lysine. In other embodiments, the amino acid is arginine.

The halide may be chlorine, bromine, or iodine, most typically chlorine. The acid addition salt of an amino acid and a halogen acid (e.g., HCl, HBr, or HI) is sometimes referred to herein as an amino acid hydrohalide. Thus one example of an amino acid hydrohalide is lysine hydrochloride. Another is glycine hydrochloride.

The zinc ion source for combination with an amino acid halide or an amino acid optionally plus halogen acid in this case is tetrabasic zinc chloride. Tetrabasic zinc chloride (TBZC) or zinc chloride hydroxide monohydrate is a zinc hydroxy compound with the formula $Zn_5(OH)_8Cl_2.H_2O$, also referred to as basic zinc chloride, zinc hydroxychloride, or zinc oxychloride. It is a colorless crystalline solid insoluble in water. One surprising advantage of the invention is that TBZC forms complexes with the amino acid more efficiently than zinc oxide.

In certain embodiments, the amount of zinc amino acid halide in the composition is 0.05 to 30% by weight of the composition. In certain embodiments, precursors, e.g., TBZC and amino acid hydrohalide, are present in amounts such that when combined into the zinc amino acid halide, the zinc amino acid halide would be present in an amount of 0.05 to 10% by weight of the composition. In either of these embodiments, the amount of the zinc amino acid halide can be varied for the desired purpose, such as a dentifrice or a mouthwash. In other embodiments, the amount of the zinc amino acid halide is at least 0.1, at least 0.2, at least 0.3, at least 0.4, at least 0.5, at least 1, at least 2, at least 3, or at least 4 up to 30% by weight of the composition. In other embodiments, the amount of the zinc amino acid halide is less than 9, less than 8, less than 7, less than 6, less than 5, less than 4, less than 3, less than 2, less than 1, less than 0.5 to 0.05% by weight of the composition. In other embodiments, the amounts are 0.05 to 5%, 0.05 to 4%, 0.05 to 3%, 0.05 to 2%, 0.1 to 5%, 0.1 to 4%, 0.1 to 3%, 0.1 to 2%, 0.5 to 5%, 0.5 to 4%, 0.5 to 3%, or 0.5 to 2% by weight of the composition.

In certain embodiments, TBZC is present in an amount of 0.05 to 10% by weight of the composition. In other embodiments, the amount of TBZC is at least 0.1, at least 0.2, at least 0.3, at least 0.4, at least 0.5, at least 1, at least 2, at least 3, or at least 4 up to 10% by weight of the composition. In other embodiments, the amount of the TBZC is less than 9, less than 8, less than 7, less than 6, less than 5, less than 4, less than 3, less than 2, less than 1, less than 0.5 to 0.05% by weight of the composition. In other embodiments, the amounts are 0.05 to 5%, 0.05 to 4%, 0.05 to 3%, 0.05 to 2%, 0.1 to 5%, 0.1 to 4%, 0.1 to 3%, 0.1 to 2%, 0.5 to 5%, 0.5 to 4%, 0.5 to 3%, or 0.5 to 2% by weight of the composition.

In certain embodiments, amino acid hydrohalide is present in an amount of 0.05 to 30% by weight. In other embodiments, the amount is at least 0.1, at least 0.2, at least 0.3, at least 0.4, at least 0.5, at least 1, at least 2, at least 3, at least 4, at least 5, at least 10, at least 15, at least 20 up to 30% by weight. In other embodiments, the amount is less than 30, less than 25, less than 20, less than 15, less than 10, less than 5, less than 4, less than 3, less than 2, or less than 1 down to 0.05% by weight of the composition.

Where precursor materials are present, they are preferably present in molar ratios approximately as required to produce the desired zinc amino acid halide, although an excess of one material or another may be desirable in certain formulations, e.g., to balance pH against other formulation constituents, to provide additional antibacterial zinc, or to provide amino acid buffer. Preferably, however, the amount of halide is limited, as constraining the level of halide somewhat encourages interaction between the zinc and the amino acid.

In some embodiments, the total amount of zinc in the composition is 0.05 to 8% by weight of the composition. In other embodiments, the total amount of zinc is at least 0.1, at least 0.2, at least 0.3, at least 0.4, at least 0.5, or at least 1 up to 8% by weight of the composition. In other embodiments, the total amount of zinc in the composition is less than 5, less than 4, less than 3, less than 2, or less than 1 to 0.05% by weight of the composition.

In certain embodiments, a molar ratio of zinc to amino acid is at least 2:1. In other embodiments, the molar ratio is at least 1:1, at least 1:2, at least 1:3, at least 1:4, 2:1 to 1:4, 1:1 to 1:4, 1:2 to 1:4, 1:3 to 1:4, 2:1 to 1:3, 2:1 to 1:2, 2:1 to 1:1, or 1:3. Above 1:4, it is expected that the zinc will be totally dissolved.

In certain embodiments, the composition is anhydrous. By anhydrous, there is less than 5% by weight water, optionally less than 4, less than 3, less than 2, less than 1, less than 0.5, less than 0.1 down to 0% by weight water.

When provided in an anhydrous composition, precursors, e.g., TBZC and amino acid hydrohalide, will not significantly react to form the zinc amino acid halide. When contacted with a sufficient amount of water, which can be in the form of saliva and/or water used to rinse the mouth during or after application of the composition, the precursors will then react to form the zinc amino acid halide, then upon further dilution, will provide the zinc-containing precipitate to the teeth.

The carrier represents all other materials in the composition other than the zinc amino acid halide complex or its precursors. The amount of carrier is then the amount to reach 100% by adding to the weight of the zinc amino acid halide, including any precursors.

The compositions of the invention may comprise various agents which are active to protect and enhance the strength and integrity of the enamel and tooth structure and/or to reduce bacteria and associated tooth decay and/or gum disease, including or in addition to the zinc-amino acid-halide complexes. Effective concentration of the active ingredients used herein will depend on the particular agent and the delivery system used. It is understood that a toothpaste for example will typically be diluted with water upon use, while a mouth rinse typically will not be. Thus, an effective concentration of active in a toothpaste will ordinarily be 5-15× higher than required for a mouth rinse. The concentration will also depend on the exact salt or polymer selected. For example, where the active agent is provided in salt form, the counterion will affect the weight of the salt, so that if the counterion is heavier, more salt by weight will be required to provide the same concentration of active ion in the final product. Arginine, where present, may be present at levels from, e.g., about 0.1 to about 20 wt % (expressed as weight of free base), e.g., about 1 to about 10 wt % for a consumer toothpaste or about 7 to about 20 wt % for a professional or prescription treatment product. Fluoride where present may be present at levels of, e.g., about 25 to about 25,000 ppm, for example about 750 to about 2,000 ppm for a consumer toothpaste, or about 2,000 to about 25,000 ppm for a professional or prescription treatment product. Levels of antibacterial agents will vary similarly, with levels used in toothpaste being e.g., about 5 to about 15 times greater than used in mouthrinse. For example, a triclosan toothpaste may contain about 0.3 wt % triclosan.

The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. In certain embodiments, the oral care composition of the invention may also contain a source of fluoride ions or fluorine-providing ingredient in amounts sufficient to supply about 25 ppm to about 25,000 ppm of fluoride ions, generally at least about 500 ppm, e.g., about 500 to about 2000 ppm, e.g., about 1000 to about 1600 ppm, e.g., about 1450 ppm. The appropriate level of fluoride will depend on the particular application. A toothpaste for general consumer use would typically have about 1000 to about 1500 ppm, with pediatric toothpaste having somewhat less. A dentifrice or coating for professional application could have as much as about 5,000 or even about 25,000 ppm fluoride. Fluoride ion sources may be added to the compositions of the invention at a level of about 0.01 wt. % to about 10 wt. % in one embodiment or about 0.03 wt. % to about 5 wt. %, and in another embodiment about 0.1 wt. % to about 1 wt. % by weight of the composition in another embodiment. Weights of fluoride salts to provide the appropriate level of fluoride ion will obviously vary based on the weight of the counterion in the salt.

In some embodiments, the compositions of the invention comprise an amino acid. In particular embodiments, the amino acid may be a basic amino acid. By "basic amino acid" is meant the naturally occurring basic amino acids, such as arginine, lysine, and histidine, as well as any basic amino acid having a carboxyl group and an amino group in the molecule, which is water-soluble and provides an aqueous solution with a pH of about 7 or greater. Accordingly, basic amino acids include, but are not limited to, arginine, lysine, citrulline, ornithine, creatine, histidine, diaminobutanoic acid, diaminoproprionic acid, salts thereof or combinations thereof. In a particular embodiment, the basic amino acids are selected from arginine, citrulline, and ornithine. In certain embodiments, the basic amino acid is arginine, for example, 1-arginine, or a salt thereof.

In various embodiments, the amino acid is present in an amount of about 0.5 wt. % to about 20 wt. % of the total composition weight, about 0.5 wt. % to about 10 wt. % of the total composition weight, for example about 1.5 wt. %, about 3.75 wt. %, about 5 wt. %, or about 7.5 wt. % of the total composition weight in the case of a dentifrice, or for example about 0.5-2 wt. %, e.g., about 1% in the case of a mouthwash.

The compositions of the invention, e.g. Composition 1 et seq. include silica abrasives, and may comprise additional abrasives, e.g., a calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4.2H_2O$, also sometimes referred to herein as DiCal) or calcium pyrophosphate; calcium carbonate abrasive; or abrasives such as sodium metaphosphate, potassium metaphosphate, aluminum silicate, calcined alumina, bentonite or other siliceous materials, or combinations thereof.

Other silica abrasive polishing materials useful herein, as well as the other abrasives, generally have an average particle size ranging between about 0.1 and about 30 microns, about between 5 and about 15 microns. The silica abrasives can be from precipitated silica or silica gels, such as the silica xerogels described in U.S. Pat. No. 3,538,230, to Pader et al. and U.S. Pat. No. 3,862,307, to Digiulio. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason. In certain embodiments, abrasive materials useful in the practice of the oral care compositions in accordance with the invention include silica gels and precipitated amorphous silica having an oil absorption value of less than about 100 cc/100 g silica and in the range of about 45 cc/100 g to about 70 cc/100 g silica. Oil absorption values are measured using the ASTA Rub-Out Method D281. In certain embodiments, the silicas are colloidal particles having an average particle size of about 3 microns to about 12 microns, and about 5 to about 10 microns. Low oil absorption silica abrasives particularly useful in the practice of the invention are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of 29% by weight averaging about 7 to about 10 microns in diameter, and an oil absorption of less than about 70 cc/100 g of silica is an example of a low oil absorption silica abrasive useful in the practice of the present invention.

The oral care compositions of the invention also may include an agent to increase the amount of foam that is produced when the oral cavity is brushed. Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of about 200,000 to about 7,000,000. In one embodiment the molecular weight will be about 600,000 to about 2,000,000 and in another embodiment about 800,000 to about 1,000,000. Polyox® is the trade name for the high molecular weight polyoxyethylene produced by Union Carbide. The polyoxyethylene may be present in an amount of about 1% to about 90%, in one embodiment about 5% to about 50% and in another embodiment about 10% to about 20% by weight of the oral care carrier component of the oral care compositions of the present invention. Where present, the amount of foaming agent in the oral care composition (i.e., a single dose) is about 0.01 to about 0.9% by weight, about 0.05 to about 0.5% by weight, and in another embodiment about 0.1 to about 0.2% by weight.

The compositions useful in the invention may contain anionic surfactants, for example:
i. water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomonoglyceride sulfate,
ii. higher alkyl sulfates, such as sodium lauryl sulfate,
iii. higher alkyl-ether sulfates, e.g., of formula $CH_3(CH_2)_m CH_2(OCH_2CH_2)_n OSO_3X$, wherein m is 6-16, e.g., 10, n is 1-6, e.g., 2, 3 or 4, and X is Na or K, for example sodium laureth-2 sulfate $(CH_3(CH_2)_{10}CH_2(OCH_2CH_2)_2OSO_3Na)$.
iv. higher alkyl aryl sulfonates such as sodium dodecyl benzene sulfonate (sodium lauryl benzene sulfonate)
v. higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

By "higher alkyl" is meant, e.g., $C_{6-30}$ alkyl. In particular embodiments, the anionic surfactant is selected from sodium lauryl sulfate and sodium ether lauryl sulfate. The anionic surfactant may be present in an amount which is effective, e.g., >0.01% by weight of the formulation, but not at a concentration which would be irritating to the oral tissue, e.g., <10%, and optimal concentrations depend on the particular formulation and the particular surfactant. For example, concentrations used or a mouthwash are typically on the order of one tenth that used for a toothpaste. In one embodiment, the anionic surfactant is present in a toothpaste at from about 0.3% to about 4.5% by weight, e.g., about 1.5%. The compositions of the invention may optionally contain mixtures of surfactants, e.g., comprising anionic surfactants and other surfactants that may be anionic, cationic, zwitterionic or nonionic. Generally, surfactants are those which are reasonably stable throughout a wide pH range. Surfactants are described more fully, for example, in U.S. Pat. No. 3,959,458, to Agricola et al.; U.S. Pat. No. 3,937,807, to Haefele; and U.S. Pat. No. 4,051,234, to Gieske et al. In certain embodiments, the anionic surfactants useful herein include the water-soluble salts of alkyl sulfates having about 10 to about 18 carbon atoms in the alkyl radical and the water-soluble salts of sulfonated monoglycerides of fatty acids having about 10 to about 18 carbon atoms. Sodium lauryl sulfate, sodium lauroyl sarcosinate and sodium coconut monoglyceride sulfonates are examples of anionic surfactants of this type. In a particular embodiment, the composition of the invention, e.g., Composition 1, et seq., comprises sodium lauryl sulfate.

The surfactant or mixtures of compatible surfactants can be present in the compositions of the present invention in about 0.1% to about 5.0%, in another embodiment about 0.3% to about 3.0% and in another embodiment about 0.5% to about 2.0% by weight of the total composition.

In various embodiments of the present invention, the compositions comprise an anticalculus (tartar control) agent. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. The invention thus may comprise phosphate salts. In particular embodiments, these salts are alkali phosphate salts, i.e., salts of alkali metal hydroxides or alkaline earth hydroxides, for example, sodium, potassium or calcium salts. "Phosphate" as used herein encompasses orally acceptable mono- and polyphosphates, for example, $P_{1-6}$ phosphates, for example monomeric phosphates such as monobasic, dibasic or tribasic phosphate; dimeric phosphates such as pyrophosphates; and multimeric phosphates, e.g., sodium hexametaphosphate. In particular examples, the selected phosphate is selected from alkali dibasic phosphate and alkali pyrophosphate salts, e.g., selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any of two or more of these. In a particular embodiment, for example the compositions comprise a mixture of tetrasodium pyrophosphate ($Na_4P_2O_7$), calcium pyrophosphate ($Ca_2P_2O_7$), and sodium phosphate dibasic ($Na_2HPO_4$), e.g., in amounts of ca. 3-4% of the sodium phosphate dibasic and ca. 0.2-1% of each of the pyrophosphates. In another embodiment, the compositions comprise a mixture of tetrasodium pyrophosphate (TSPP) and sodium tripolyphosphate (STPP)($Na_5P_3O_{10}$), e.g., in proportions of TSPP at about 1-2% and STPP at about 7% to about 10%. Such phosphates are provided in an amount effective to reduce erosion of the enamel, to aid in cleaning the teeth, and/or to reduce tartar buildup on the teeth, for example in an amount of 2-20%, e.g., ca. 5-15%, by weight of the composition.

The oral care compositions of the invention may also include a flavoring agent. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint. The flavoring agent may be incorporated in the oral composition at a concentration of about 0.1 to about 5% by weight e.g. about 0.5 to about 1.5% by weight.

The oral care compositions of the invention may also include additional polymers to adjust the viscosity of the formulation or enhance the solubility of other ingredients. Such additional polymers include polyethylene glycols, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts.

Silica thickeners, which form polymeric structures or gels in aqueous media, may be present. Note that these silica thickeners are physically and functionally distinct from the particulate silica abrasives also present in the compositions, as the silica thickeners are very finely divided and provide little or no abrasive action. Other thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate can also be used as component of the thickening composition to further improve the composition's texture. In certain embodiments, thickening agents in an amount of about 0.5% to about 5.0% by weight of the total composition are used.

The compositions of the invention may include an anionic polymer, for example in an amount of from about 0.05 to about 5%. Such agents are known generally for use in dentifrice, although not for this particular application, useful in the present invention are disclosed in U.S. Pat. Nos. 5,188,821 and 5,192,531; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 300,000 to about 800,000. These copolymers are available for example as Gantrez. e.g., AN 139 (M.W. 500,000), AN 119 (M.W. 250,000) and preferably S-97 Pharmaceutical Grade (M.W. 700,000) available from ISP Technologies, Inc., Bound Brook, N.J. 08805. The enhancing agents when present are present in amounts ranging from about 0.05 to about 3% by weight. Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid. Another useful class of polymeric agents includes polyamino acids containing proportions of anionic surface-active amino acids such as aspartic acid, glutamic acid and phosphoserine, e.g. as disclosed in U.S. Pat. No. 4,866,161 Sikes et al.

The oral compositions may comprise significant levels of water. Water employed in the preparation of commercial oral compositions should be deionized and free of organic impurities. The amount of water in the compositions includes the free water which is added plus that amount which is introduced with other materials.

Within certain embodiments of the oral compositions, it is also desirable to incorporate a humectant to prevent the composition from hardening upon exposure to air. Certain humectants can also impart desirable sweetness or flavor to dentifrice compositions. Suitable humectants include edible polyhydric alcohols such as glycerine, sorbitol, xylitol, propylene glycol as well as other polyols and mixtures of these humectants. In one embodiment of the invention, the principal humectant is glycerin, which may be present at levels of greater than 25%, e.g. 25-35% about 30%, with 5% or less of other humectants.

In addition to the above-described components, the embodiments of this invention can contain a variety of optional dentifrice ingredients some of which are described below. Optional ingredients include, for example, but are not limited to, adhesives, sudsing agents, flavoring agents, sweetening agents, additional antiplaque agents, abrasives, and coloring agents. These and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference.

Unless stated otherwise, all percentages of composition components given in this specification are by weight based on a total composition or formulation weight of 100%.

Unless otherwise specifically identified, the ingredients for use in the compositions and formulations of the present invention are preferably cosmetically acceptable ingredients. By "cosmetically acceptable" is meant suitable for use in a formulation for topical application to human skin. A cosmetically acceptable excipient, for example, is an excipient which is suitable for external application in the amounts and concentrations contemplated in the formulations of this invention, and includes for example excipients which are "Generally Recognized as Safe" (GRAS) by the United States Food and Drug Administration.

The compositions and formulations as provided herein are described and claimed with reference to their ingredients, as is usual in the art. As would be evident to one skilled in the art, the ingredients may in some instances react with one another, so that the true composition of the final formulation may not correspond exactly to the ingredients listed. Thus, it should be understood that the invention extends to the product of the combination of the listed ingredients.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

EXAMPLES

Example 1

Zn concentration of TBZC is compared TBZC and various amino acids. Ingredients are dispersed in water, equilibrated for 1 h, and the supernatant analyzed for free $Zn^{2+}$ by atomic absorption. Table 1 shows comparison of free Zn concentration of TBZC and TBZC mixed with different amino acids.

TABLE 1

|  | Free Zn (ppm) |
| --- | --- |
| TBZC + Arginine (4 + 4%) | 1819.00 |
| TBZC + Lysine-HCl (4 + 4%) | 6000.00 |
| TBZC + Lysine (4 + 4%) | 5000.00 |
| TBZC (4%) | 64.80 |

The data described in Table 1 (above) demonstrates the dramatic increase in the solubility of zinc when an amino acid is added. For example, solubility increases 28 times when arginine is added and near 100 times when lysine hydrochloride is mixed with TBZC.

Example 2

Stable solutions of TBZC-amino acid complexes are prepared for further testing, using lysine, glycine, and arginine as the amino acids.

A. TBZC-Lysine: Sample A1, TBZC-Lysine is prepared as follows: At room temperature, 2.7601 g (0.005 mol) of TBZC powder is slowly added into 1M of lysine aqueous solution (0.05 mol of lysine in 50 ml deionized water). The mixture is stirred for 3 hours. Unreacted TBZC is removed by centrifuging followed by filtering through a 0.45 µm membrane. Zinc concentration is determined by atomic absorption spectroscopy after acid digestion.

TABLE 2

|  | TBZC | Lysine |
| --- | --- | --- |
| Amount added | 2.7601 g, 0.005 mol | 7.3101 g, 0.05 mol |
| pH of final solution | 10.8 | |
| Zn content of stock solution (w/w %) | 1.95% | |
| Stock:Water ratio (v/v) for treatment | 1:8 | |

The procedure is repeated to form Sample A2, which has slightly lower zinc content, due to experimental variation:

TABLE 3

|  | TBZC | Lysine |
| --- | --- | --- |
| Amount added | 2.7612 g, 0.005 mol | 7.3097 g, 0.05 mol |
| pH of final solution | 10.7 | |
| Zn content of stock solution {w/w %) | 1.44% | |
| Stock:Water ratio (v/v) for treatment | 1:8 | |

B. TBZC-Glycine: Sample B, TBZC-glycine, is prepared as follows: At room temperature, 2.7599 g (0.005 mol) of TBZC powder is slowly added into 1M of lysine aqueous solution (0.05 mol of glycine in 50 ml deionized water). The mixture is stirred for 3 hours. Unreacted TBZC is removed by centrifuging followed by filtering through a 0.45 µm membrane. Zinc concentration is determined by atomic absorption spectroscopy after acid digestion.

TABLE 4

|  | TBZC | Glycine |
| --- | --- | --- |
| Amount added | 2.7599 g, 0.005 mol | 7.3540 g, 0.05 mol |
| pH of final solution | 6.7 | |
| Zn content of stock solution (w/w %) | 2.78% | |
| Stock:Water ratio {v/v) for treatment | 1:8 | |

C. TBZC-Arginine: Sample C1, TBZC-arginine, is prepared as follows. TBZC is added into arginine aqueous solution (0.05 mol of arginine in 50 ml deionized water) at about 37° C. under stirring. The mixture is stirred for about 2 hours followed by centrifuging at high speed to separate unreacted TBZC. The supernatant is filtered through a 0.45 µm membrane. Zinc concentration is determined by atomic absorption spectroscopy after acid digestion.

TABLE 5

|  | TBZC | Arginine |
| --- | --- | --- |
| Amount added | 2.7608 g, 0.005 mol | 8.7104 g, 0.05 mol |
| pH of final solution | 11.3 | |
| Zn content of stock solution (w/w %) | 2.50% | |
| Stock:Water ratio (v/v) for treatment | 1:8 | |

The procedure is repeated to form Sample C2, this time using a higher concentration of TBZC, and also a higher final dilution of water.

TABLE 6

|  | TBZC | Arginine |
| --- | --- | --- |
| Amount added | 5.5186 g, 0.01 mol | 8.7145 g, 0.05 mol |
| pH of final solution | 10.4 | |
| Zn content of stock solution (w/w %) | 1.53% | |
| Stock:Water ratio (v/v) for treatment | 1:15 | |

Example 3

The TBZC-amino acid solutions are shown to be effective in occluding dentinal tubules when applied to the teeth and diluted to trigger precipitation. This deposition and tubule occlusion should reduce sensitivity and provide a reservoir of zinc to help protect the enamel against erosion and bacterial colonization.

The dentine slices are prepared by cutting whole human tooth into thin dentine sections of about 800 microns in thickness, designating a test side, sanding said test side using a sandpaper of about 600 grit to remove any enamel on said test side, polishing said test side using a Buehler polishing cloth and 5 micron Buehler aluminum oxide, acid-etching said dentine section in 1% (by weight) citric acid solution for about 20 seconds, sonicating said dentine section for 10 minutes, and storing said dentine section in phosphate buffered saline (PBS, pH 7.4, Gibco Cat. No. 10010)."

The thin slices of human dentin sections are imaged on the confocal microscope for baseline characterization. Top view images are taken in XYZ mode, and side view images are taken in XZY mode. Typical images are taken with a 50× objective lens, and with ×4 digital magnification. When a more global view is desired at lower magnification, the images are taken at ×1 digital magnification.

The thin slices of human dentin sections are treated using the respective treatment solutions following the procedures as set forth below. The three distinct treatment procedures include A), treatments for 1 hour using the test solutions (TBZC-arginine, TBZC-glycine and TBZC-lysine), B) treatment using an alternative method using TBZC-lysine, and C) treatments with shorter durations and more repeats. The treated thin slices are examined under the confocal microscope for signs of occlusion and deposition on the surface. Repeat treatments are made on the treated discs using the same or substantially same treatment procedure as the prior treatment, the same TBZC-amino acid solution, and in most cases, treatment solutions of the same batches. Confocal images are taken to monitor the progress of additional occlusion and deposition after one or more repeat treatments.

A. One Hour Treatments Using TBZC-Arginine, TBZC-Lysine, and TBZC-Glycine: The dentin discs are added after the stock solutions of the TBZC-amino acids are mixed with water. The stock solutions of TBZC-amino acids are first mixed in a vial with the appropriate amount of water as set forth in Tables 2, 3, 4, 5 and 6 (for example, 1 mL of stock solution with 8 mL of deionized water for a system with 1:8 stock:water ratio). Within seconds, the dentin slice is added to the vial and the vial is capped and stored in an incubator at 37° C. for one hour for treatment. At the conclusion of the treatment, the vial is removed from the incubator, and the liquid and precipitate, if any, are removed using a pipettor. The dentine disc is rinsed for 4 times, each time using 1 mL of PBS (pH=7.4) solution. The dentine disc is dried using a tissue.

The three different TBZC-amino acids complex systems with similar zinc concentration generate different amounts of precipitation at different rates. TBZC-lysine produced precipitates immediately upon or within seconds after initial mixing, and white precipitates are observed at the bottom of the vials at the end of the 1 hour incubation. TBZC-arginine does not produce precipitation upon initial mixing, but the system turns cloudy and some precipitation can be observed at the bottom of the vials at the end of the 1 hour incubation. TBZC-glycine does not generate any precipitation, and the solution remains transparent and clear throughout the 1 hour incubation.

TBZC-arginine substantially completely occludes the dentin tubules and forms a substantially complete coverage on the surface of the dentin slice, after the 1 hour treatments. Two batches of the complex solutions (C1 and C2 from Example 2 above) show no qualitative differences in efficacy.

Evolution of confocal images indicates progressive deposition and occlusion. Baseline images indicate open tubules and clean surface between the openings. Upon a single treatment, significant tubule occlusion is observed, as well as substantial deposition between the tubule openings. Upon the second and third treatments, substantially all tubule openings are occluded and substantially all surface area between the tubule openings are covered by deposits. Side view images indicate the presence of some deposits with thickness of upper-single-digit microns or higher. The experiments are carried out on two separate dentin discs, and the results are qualitatively the same.

TBZC-lysine is also shown to occlude the dentine tubules substantially and form considerable surface deposits, particularly after repeated treatments, each for 1 hour.

Confocal images again show the progression. Baseline images indicate open tubules and clean surface between the tubule openings. After one treatment, some deposits are observed between tubule openings, and some tubules are at least partially occluded. After two treatments, the results are not qualitatively different from that after the first treatment. While the two discs, representing duplicate experiments, qualitatively show no different results between them for the first two treatments, the results differ more significantly between the two dentin discs after the third treatment. On one disc, there are substantial surface deposits with some occlusion. On the second disc, there are deposits completely covering the surface, as well as complete occlusion. The significant increase in deposition/occlusion with repeated treatments suggests that the surface of the disc is conditioned by prior treatments and could receive more deposits/occludants during subsequent treatments. Similar results are observed using solutions A1 and A2 from Example 2 above.

TBZC-glycine is shown by the confocal images to provide limited occlusion and surface deposits upon repeated treatments, each for 1 hour. While TBZC-glycine is not without effect, the deposition is not as substantial as that for TBZC-lysine or TBZC-arginine. Baseline images indicate open tubules and clean surface between the tubule openings. After one treatment, the images indicate little, if any, occlusion and surface deposits. The same is true after two treatments. After three treatments, both discs show some deposits. Therefore, TBZC-glycine has more limited capability of occluding dentin tubules and forming deposits on the surface, at least in the concentrations tested, compared to TBZC-arginine or TBZC-lysine.

B. Alternative Treatment Procedure using TBZC-Lysine: In the alternative procedure, specifically for TBZC-lysine samples, the dentin discs are added first to the TBZC-lysine stock solution, and the appropriate amount of water is subsequently added. The rest of the treatment procedure is the same as that in the default procedure for one hour treatment.

The employment of the alternative method is motivated by the observation that precipitation takes place within seconds after TBZC-lysine stock solution and the entire amount of water is mixed. In this alternative treatment method, the disc is allowed to come in contact with the TBZC-lysine stock solution before water is subsequently added. This change should allow interaction of the disc surface with the nascent precipitates, possibly leading to more significant surface deposition and occlusion. On the other hand, it would be conceivable that the stock solution might dissolve some of the existing surface deposits and/or occluding particles upon repeated treatments.

The confocal images for the dentin discs treated using this alternative method indicate the success of surface deposition and occlusion. It can be seen that significant surface deposition and tubule occlusion takes place after the alternative treatments. This supports a regimen of applying a more concentrated solution of the TBZC-amino acid complex, then diluting to trigger precipitation.

C. Repeat Treatments with Shorter Durations (one minute): In this repeat treatment with shorter durations, the dentin discs are treated for one minute each time, instead of one hour. In addition, more repeat treatments are conducted. Otherwise, the treatment procedure is the same as the one set forth in section A above.

As stated earlier, precipitation takes place immediately when TBZC-lysine is mixed with the appropriate amount of water. The quick reaction in the TBZC-lysine system enables a short yet effective treatment, which is more preferable than the 1-hour treatment involved in the default and the alternative treatment methods discussed above. It is contemplated that the short duration, such as 1 minute each time, coupled with multiple repeats to make up for the possible loss of efficacy in each treatment, may provide a typical user with a more pleasant experience and better compliance.

Confocal images of a dentin disc treated for 3 times and 6 times using this method confirms the value of this treatment method. Significant surface deposition and occlusion are observed after 3 treatments, each lasting only 1 minute. Similar results are seen after 6 treatments. Images taken at lower resolution indicate that the phenomena are global.

Therefore, short treatment durations can be employed for TBZC-lysine. The treatment duration may be further reduced below 1 minute if desired without significant impediment on the efficacy.

While the above tests show the efficacy of the TBZC-amino acid at a set concentration, many other concentrations also work to generate precipitation and cause surface deposition. It is noted that even in the absence of formation of precipitates visible to the naked eyes (due to an unfavorable concentration and/or short treatment duration), surface deposition and/or tubule occlusion can result from the formation of microscopic particles. Such action may necessitate more than 3 repeat treatments to achieve a substantial or complete surface coverage and tubule occlusion. In this regard, the operable concentration of the active and the operable treatment duration enjoy wider ranges than what can be inferred based on the above-mentioned examples, and the subsequent three paragraphs.

Using Sample A1 (TBZC-lysine), some precipitation can be formed within an hour with a 1:1 dilution (0.975 wt % zinc), and significant amounts can be found in 1:2, 1:3, 1:4, 1:5, 1:6, 1:7, 1:8 and 1:9 dilutions (0.65%, 0.488%, 0.39%, 0.325%, 0.278%, 0.244%, 0.217%, 0.195%, by weight, zinc respectively). Higher dilutions are also expected to work, and precipitation typically happens faster in higher dilutions. Thus, TBZC-lysine samples with dilutions 1:1 and above (with a zinc concentration of about 0.975% and lower) will produce a precipitate and result in deposition.

Using Sample A2 (TBZC-lysine), precipitation can be found with dilutions of 1:6 and 1:7 (0.205% and 0.18% of zinc by weight) and higher dilutions are expected to work as well. Thus, TBZC-lysine samples with zinc concentrations of 0.205 wt % and lower will work in producing precipitation and deposition. The difference from Sample A1 is due to sample variation.

Using Sample C2 (TBZC-arginine), precipitation can be found with dilutions 1:5, 1:11, 1:12, 1:13, and 1:14 (0.255%, 0.128%, 0.118%, 0.109%, and 0.102% of zinc by weight). Higher dilutions are expected to work as well. Precipitation typically happens faster in higher dilutions. Thus, TBZC-arginine samples with zinc concentration of 0.255 wt % or lower will work in producing precipitation and deposition.

The precipitates contain zinc oxide and other zinc-containing species (such as zinc hydroxide), as well as the corresponding amino acid. The amino acid content is particularly high if the precipitates are not rinsed with water.

Without wishing to be bound by the theory, it is hypothesized that the deposit on the dentine surface is comprised of a dual-component structure, like in the form of a core-shell, or dual layer manner. The outer layer is composed of amorphous zinc species, which is not ZnO. The outer layer also contains amino acid. The outer layer can be readily removed through simple rinsing with water. What lies under the outer layer is a component that is comprised of primarily ZnO as well as amino acids.

The more complex structure brings the concept of controlled release to a new level. Originally, the concept of controlled release is invoked because the zinc can be released from ZnO over time, as well as amino acid from the deposits. Now, with this new structure, we have an outer layer with more soluble zinc and amino acid, and an inner layer with a lower solubility.

A unique aspect of the present invention is the provision of a controlled release system and a method for continued release of zinc ions and amino acids over an extended period of time. The occluding particles and the surface deposits can release zinc ions and amino acids into saliva or plaque fluid over an extended period of time, providing oral care benefits for a much longer period of time than a typical existing formulation.

The structure of the occluding particles and surface deposits is particularly suitable for controlled release of zinc ions and amino acids. As described above, it is hypothesized that these particles and deposits have an outer layer comprising of largely non-ZnO zinc species and amino acid, and an inner layer comprising of largely ZnO and some amino acids. The outer layer can be readily dissolved during rinsing, thus providing a source of zinc and amino acid for quick release. This is likely due to two factors. First, the non-ZnO zinc species might have a solubility higher than that of ZnO. Second, amino acids, such as arginine and lysine, can enhance the solubility of zinc containing compounds. The inner layer can be dissolved over a long period of time, thus providing a source of zinc and amino acid for more sustained release.

TBZC-amino acid can promote biofilm aggregation. Aggregates do not attach efficiently to dental surface and therefore can be more easily removed. The promotion of biofilm aggregation is thus an additional biologically relevant benefit.

Example 4

An exemplary dentifrice of the present invention, comprising TBZC-lysine, 1450 ppm fluoride, and phosphates is described below in Table 7.

TABLE 7

| INGREDIENT | WEIGHT % |
| --- | --- |
| PEG600 | 3 |
| CMC-7 | 0.65 |
| Xanthan | 0.2 |
| Sorbitol | 27 |
| Glycerin | 20 |
| Saccharin | 0.3 |
| Tetrasodium pyrophosphate | 0.5 |
| Calcium pyrophosphate | 0.25 |
| Sodium phosphate dibasic | 3.5 |
| Sodium fluoride (to provide 1450 ppm fluoride) | 0.32 |
| Titanium dioxide | 0.5 |
| Abrasive silica | 8 |
| Thickener silica | 8 |
| Sodium lauryl sulfate | 1.5 |
| Flavoring | 1.2 |
| TBZC-Lysine | 7 (TBZC [2] + Lysine [5]) |
| Water | QS |

Example 5

An exemplary mouthwash formulation of present invention is described in Table 8 (below).

TABLE 8

| INGREDIENT | WEIGHT % |
| --- | --- |
| Sorbitol | 5.5 |
| Glycerin | 7.5 |
| Propylene glycol | 7 |
| Sodium saccharin | 0.02 |
| Citric acid (anhydrous) | 0.05 |
| TBZC | 0.028 |
| L-Lysine | 0.05 |
| Flavor/dye | 0.12 |
| Potassium sorbate | 0.05 |

TABLE 8-continued

| INGREDIENT | WEIGHT % |
| --- | --- |
| Cocamidopropyl betaine | 1 |
| Water | QS |
| TOTAL | 100 |

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the scope of the invention should be construed broadly as set forth in the appended claims.

The invention claimed is:

1. An oral care composition comprising a zinc-amino acid-halide complex; wherein the halide is chloride and wherein the complex is selected from the group consisting of $ZnLys_3Cl_2$, in an octahedral geometry; $[Zn(C_6H_{14}N_2O_2)_2 Cl]^+Cl^-$, in a distorted square pyramid geometry; and $ZnOLys_2$, in a pyramid geometry, and combinations thereof.

2. The composition of claim 1, wherein the amount of zinc is 0.05-4% by weight.

3. The composition of claim 1, wherein the complex is solubilized in the oral care composition, but provides a zinc precipitate upon dilution with saliva and/or rinsing.

4. The composition of claim 1, in the form of a toothpaste, gel, mouthwash, powder, cream, strip, or gum.

5. The composition of claim 1, in an orally acceptable base.

6. The composition of claim 1, further comprising an effective amount of a fluoride ion source.

7. The composition of claim 1 further comprising an orally acceptable base comprising ingredients selected from one or more of abrasives, buffering agents, humectants, surfactants, thickeners, gum strips or fragments, breath fresheners, flavoring, fragrance, coloring, antibacterial agents, whitening agents, agents that interfere with or prevents bacterial attachment, calcium sources, phosphate sources, orally acceptable potassium salts, and anionic polymers.

8. The composition of claim 1 wherein the pH of the composition is from pH 6 to pH 8.

9. A method of manufacturing an oral care composition according to claim 1, comprising the step of reacting tetrabasic zinc chloride with lysine to form a complex.

10. A method of treating or reducing dental enamel erosion, cleaning the teeth, reducing bacterially-generated biofilm and plaque, reducing gingivitis, inhibiting tooth decay and formation of cavities, and/or reducing dentinal hypersensitivity comprising applying a composition according to claim 1 to the oral cavity of a subject in need thereof.

* * * * *